United States Patent [19]

Ulrich

[11] Patent Number: 5,425,732
[45] Date of Patent: Jun. 20, 1995

[54] IMPLANT FOR INTERNAL FIXATION, PARTICULARLY SPONDYLODESIS IMPLANT

[76] Inventor: Heinrich Ulrich, Galgenbergweg 28, Ulm/Donau, Germany

[21] Appl. No.: 107,809
[22] PCT Filed: Jan. 13, 1993
[86] PCT No.: PCT/DE93/00033
    § 371 Date: Aug. 20, 1993
    § 102(e) Date: Aug. 20, 1993
[87] PCT Pub. No.: WO93/13722
    PCT Pub. Date: Jul. 22, 1993

[30] Foreign Application Priority Data
Jan. 16, 1992 [DE] Germany ............ 42 00 905.7

[51] Int. Cl.⁶ .................................. A61B 17/70
[52] U.S. Cl. ...................................... 606/61
[58] Field of Search ............... 606/53, 54, 59, 60, 606/61

[56] References Cited

U.S. PATENT DOCUMENTS 5,047,029 9/1991 Aebi et al. .................. 606/61
5,084,048 1/1992 Jacob et al. ................. 606/61

FOREIGN PATENT DOCUMENTS 0348581 1/1990 European Pat. Off. ....... 606/61
0408489 1/1991 European Pat. Off. ....... 606/61

*Primary Examiner*—Tamara L. Graysay
*Attorney, Agent, or Firm*—Herbert Dubno; Yuri Kateshov

[57] ABSTRACT

The implant has at least two connection pieces guided on spindles relatively to each other and adjustable with respect to their distance from each other and resetting screws for which for the fastening of the connection pieces to the bones, bone segments or vertebrae, receiving spaces are provided in the connection pieces, each of the resetting screws is guided in the respective receiving space so that it can slide in the longitudinal screw direction and is transversely pivotable thereto. Each of the receiving elements is equipped with a respective clamping mechanism actuatable by a clamping member which in the clamped position locks the resetting screw against displacement as well as pivoting in the receiving space.

6 Claims, 4 Drawing Sheets

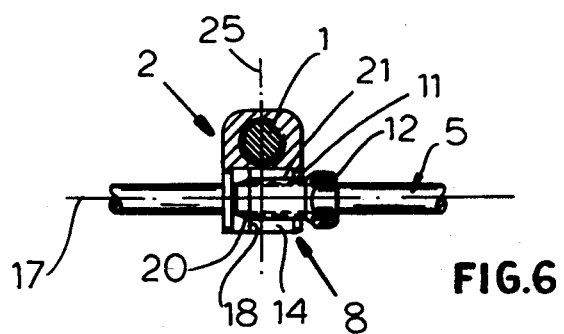
FIG.6
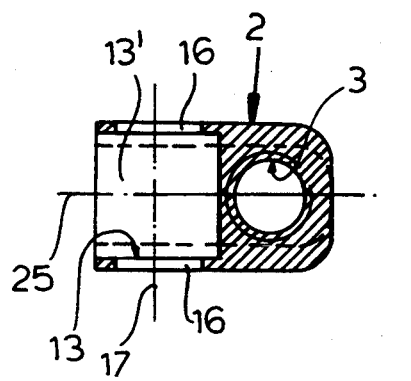 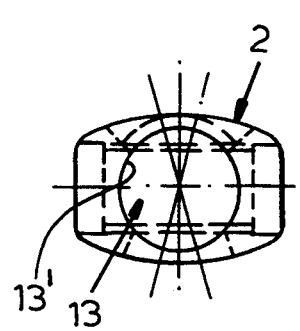 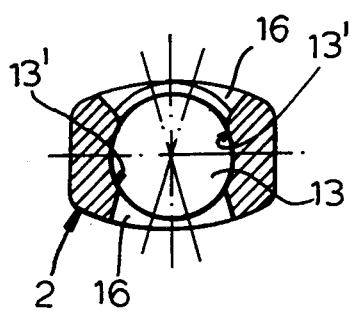
FIG.10  FIG.8  FIG.9
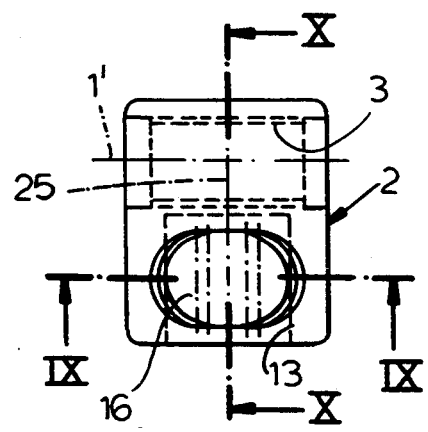
FIG.7

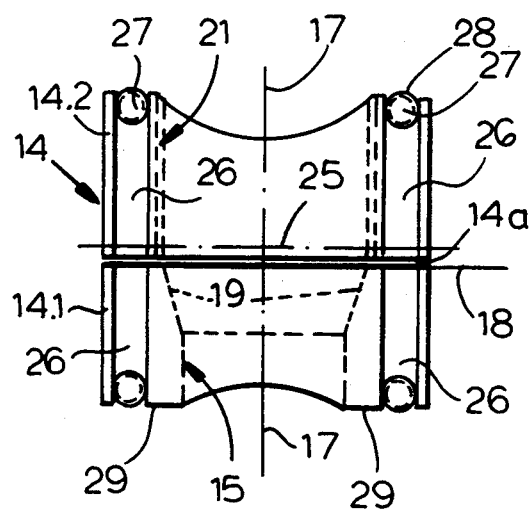
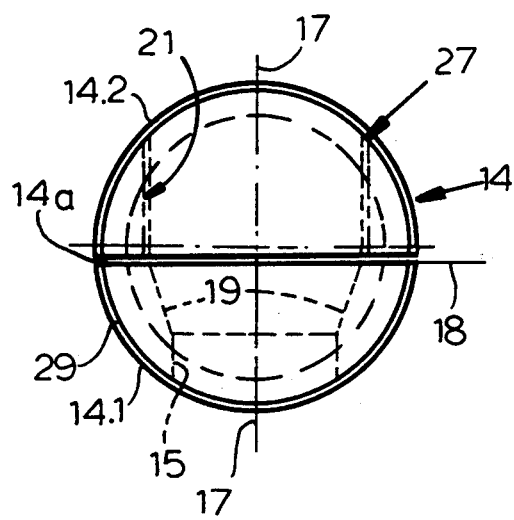
FIG.11  FIG.13
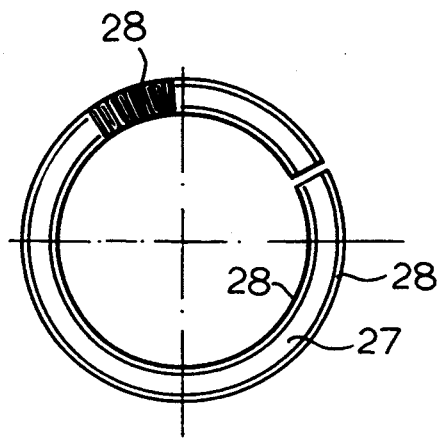
FIG.12
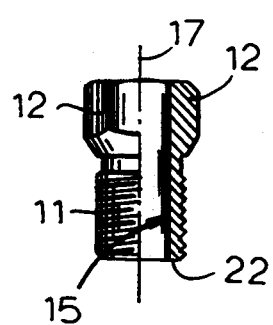
FIG.14
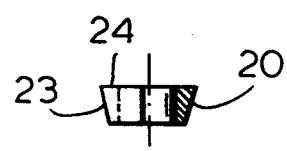
FIG.15
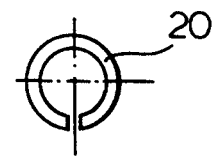
FIG.16

IMPLANT FOR INTERNAL FIXATION, PARTICULARLY SPONDYLODESIS IMPLANT

CROSS REFERENCE TO RELATED APPLICATIONS

This application is a national phase application corresponding to PCT/DE 93/00033 filed 13 Jan. 1993 and based, in turn, upon a German application P 4200905.7 filed 16 Jan. 1992 under the International Convention.

SPECIFICATION

FIELD OF THE INVENTION

The present invention relates to an implant for the correction and fixation to each other of two bones or bone segments, particularly a spondylodesis implant for the correction and fixation of the position of vertebrae with respect to each other. The invention especially relates to an apparatus of this type having at least two connection pieces guided relatively to each other and adjustable with respect to their distance from each other and with resetting screws which can be screwed into the bones or bone segments, particularly vertebrae, and for which receiving spaces are provided in the connection pieces for the purpose of fastening the connection pieces to the bones or bone segments, especially vertebrae.

BACKGROUND OF THE INVENTION

Spondylodesis implants of this kind are known in various embodiments for instance from DE 31 32 520 C2 or DE 33 06 657 C2 and differ from each other by the type and manner of the relative guiding and distance adjustment of the connection pieces, as well as by design of the receiving pieces for the resetting screws provided at the connection piece. It is common to all these known embodiments that the force-locking between the connection pieces and the resetting screws is basically achieved through the screw heads, which presumes that the resetting screws must have a precisely defined length for each particular case. This insures that within the limits of the acceptable maximal, respectively the required minimal depth of engagement the head of the resetting screw is each time in the correct position for being received in the connection pieces.

Therefore the resetting screws need not only be stored in a variety of lengths, but also must be selected in the precisely correct length prior to being screwed in, which is cumbersome and can create complications. Although it is already known to avoid these drawbacks by using headless resetting screws, so-called SCHANZ screws, which adjacent to the threaded shaft portion have a longer, smooth shaft segment to be shortened to the respective required length after implant, problems arise in these cases when the resetting screws have to be connected rigidly enough for the fixation with the connection pieces, especially then when the inclined position of the resetting screws has to be taken into consideration with respect to the mutual adjustment direction of the connection pieces.

OBJECT OF THE INVENTION

It is the object of the invention to provide an improved implant of the aforementioned kind so that the resetting screws can be reliably fastened in the receiving elements provided at the connection pieces in a quick and handy manner, to a large extent independently of their engagement depth and position on the bone or vertebra.

SUMMARY OF THE INVENTION

According to the invention, this object is achieved in the implant or bone-fixing device of the aforementioned kind by mounting the resetting screws in the respective receiving elements so that they can slide in the longitudinal direction of the screw and are guided to be transversely swingable thereto. The receiving element is equipped with a clamping device actuatable through a clamping member, which in its clamping position secures the resetting screw in the receiving element against sliding, as well as pivoting.

With the device of the invention it becomes possible to keep to a minimum the influence of the receiving element on the positioning of the resetting screw on the bone, namely its engagement depth and direction, since when the clamping device is still open the setting screw is slidable, as well as pivotable in the receiving element. However these movement possibilities are simultaneously blocked, i.e. the resetting screws and the connection piece are rigidly connected to each other, as soon as the clamping member is correspondingly activated and the clamping device becomes effective.

An embodiment of the invention particularly preferred from the constructive point of view has in the connection piece, a pivot opening for a link body containing a guide channel for the resetting screw. The link body reaches on both sides into openings provided in the walling of the connection piece. The link body is divided in two across the axis of the guide channel and in one of the two parts a conical seat coaxial with the guide channel is formed. A peripherally slotted clamping ring is located at the seat and surrounds the resetting screw. The clamping member in clamping position braces the two link body parts in the pivot opening against the opening surface and the clamping ring in the conical seat against the resetting screw.

This concurrent clamping of the link body parts on the one hand and of the clamping ring on the other hand can be achieved in a particular advantageous manner by having the conical seat with its enlarged end abut in the gap between the two link body parts and by providing in the link body part opposing the gap a threaded bore running coaxially with the guide channel. A threaded sleeve constitutes a portion of the guide channel and is engaged in the link body and pushes against the clamping ring in the conical seat and which projects outwards through the opening at it other end, thus being accessible for actuation.

Advantageously the clamping ring has an outer conical surface fitting the conical seat and the rim of the clamping ring facing the threaded sleeve has an outer diameter at least as large as the threaded sleeve. This makes it possible for the threaded sleeve to always rest only against the clamping ring during tightening, but never directly against the link body part equipped with the conical seat.

As a rule it is sufficient for the resetting screws to be pivotable with respect to the connection piece about one axis only. In this case the pivot openings and the link body should be cylindrical, with the cylinder axis being perpendicular to the axis of the guide channel. On both sides of the guide channel, at the outer peripheral surface of the link body, in peripheral grooves coaxial with the cylinder axis peripherally slotted spring rings can be embedded, the rings being outwardly provided with crossribbing and projecting slightly radially with the ribs over the cylindrical circumference of the link body.

When the link body parts are braced the ribs can press themselves on the one hand into the cylindrical peripheral surface of the pivot opening and on the other hand into the walling of the ring grooves, thereby forming a particularly rigid and reliable lock securing the link body against rotation. The crossribbing can be done in the simplest manner by providing the spring ring with threading.

The swingability of the link body about a single axis is particularly advisable in implants where the guiding of the connection piece is achieved by means of a spindle, about whose axis the connection piece can rotate and is thereby capable of adjusting to the inclined position of the resetting screws corresponding to its rotatability. In this case the cylindrical axis of the link body is preferably perpendicular to the axis of the spindle.

BRIEF DESCRIPTION OF THE DRAWING

The above and other objects, features, and advantages will become more readily apparent from the following description, reference being made to the accompanying drawing in which:

FIG. 6 is a section in the direction IV—IV through the implant according to FIGS. 1 to 5;

FIG. 7 is a top view only of the connection piece of the object in FIG. 6;

FIG. 8 is a lateral view of the connection piece of FIG. 7 in the direction of the therein indicated arrow VIII;

FIG. 9 is the section IX—IX in FIG. 7;

FIG. 10 is the section X—X in FIG. 7;

FIG. 11 is the link body of the object in FIG. 6 together with the spring rings, in a lateral view;

FIG. 12 is the spring rings in FIG. 11 in an axial view;

FIG. 13 is the link body of FIG. 11 in an axial view;

FIG. 14 is the threaded sleeve;

FIG. 15 is the clamping ring of the object of FIG. 6, partially in a lateral view, partially in section; and FIG. 16 is an axial view of the clamping ring according to FIG. 15.

SPECIFIC DESCRIPTION

FIGS. 1 to 5 show spondylodesis implants wherein the connection pieces 2 are guided by threaded spindles 1 and which are adjustable regarding their distance from each other by rotating the threaded spindle 1.

Figure 1:
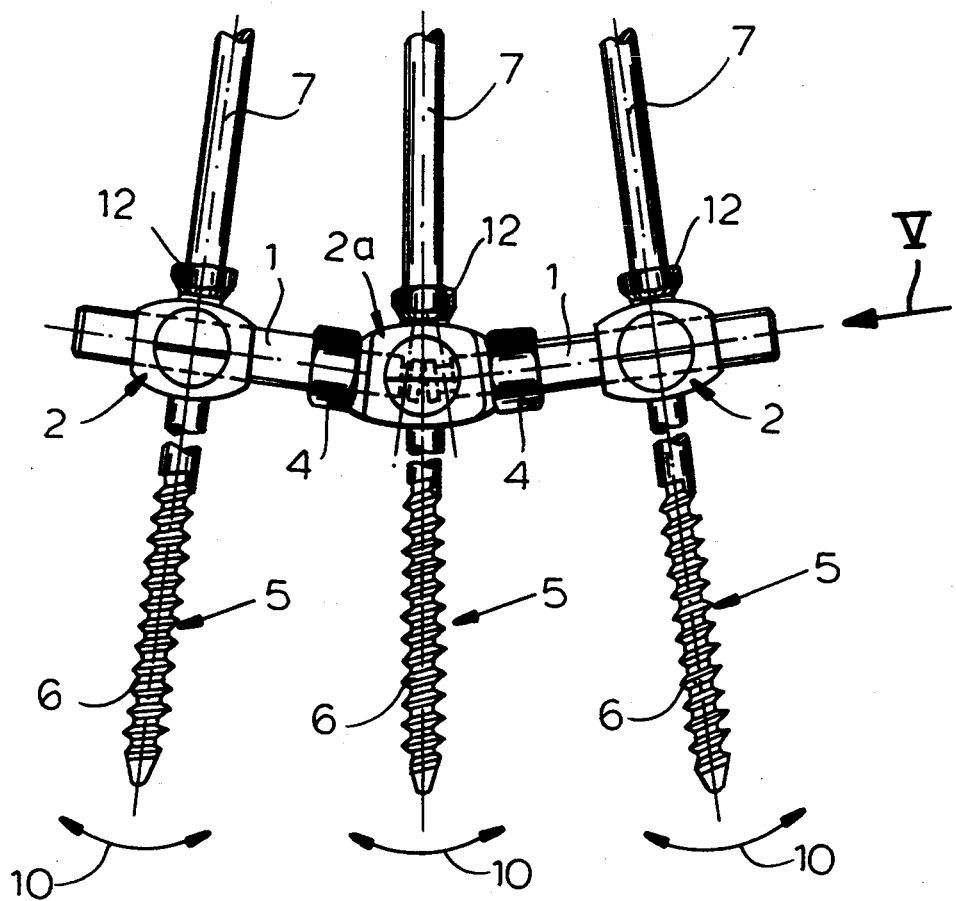
FIG. 1 is a lateral view of a spondylodesis implant according to
the invention.
Figure 2:
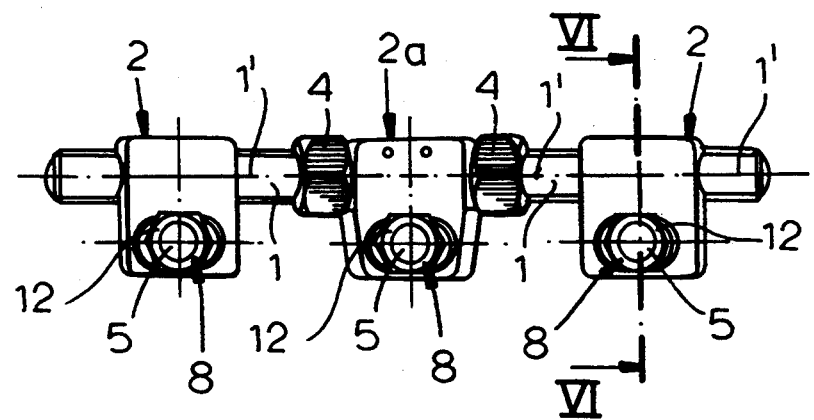
FIG. 2 is a top view of the implant according to FIG. 1.

In the embodiment according to FIGS. 1 and 2 a total of three connection pieces 2, 2a is provided, whereby the middle connection piece 2a serves for supporting the two lateral threaded spindles 1 rotatably and axially stable, which is not shown in detail in the drawing.

The two threaded spindles 1 are screwed into threaded bores 3 (FIG. 10) of the lateral connection pieces, so that by turning the threaded spindles 1 about the respective axes 1', which for this purpose are equipped with a hexagonal collar 4 for the application of an appropriate key, the two lateral connection pieces 2 can be independently adjusted.

In order to connect the connection pieces 2 with the respective vertebra not shown in the drawing, bone resetting screws 5 are used, which can be screwed into the vertebra with their threaded portion 6 and are held with their smooth, threadless portion 7 in a receiving element generally marked with 8 of the connection pieces 2.

Figure 3:
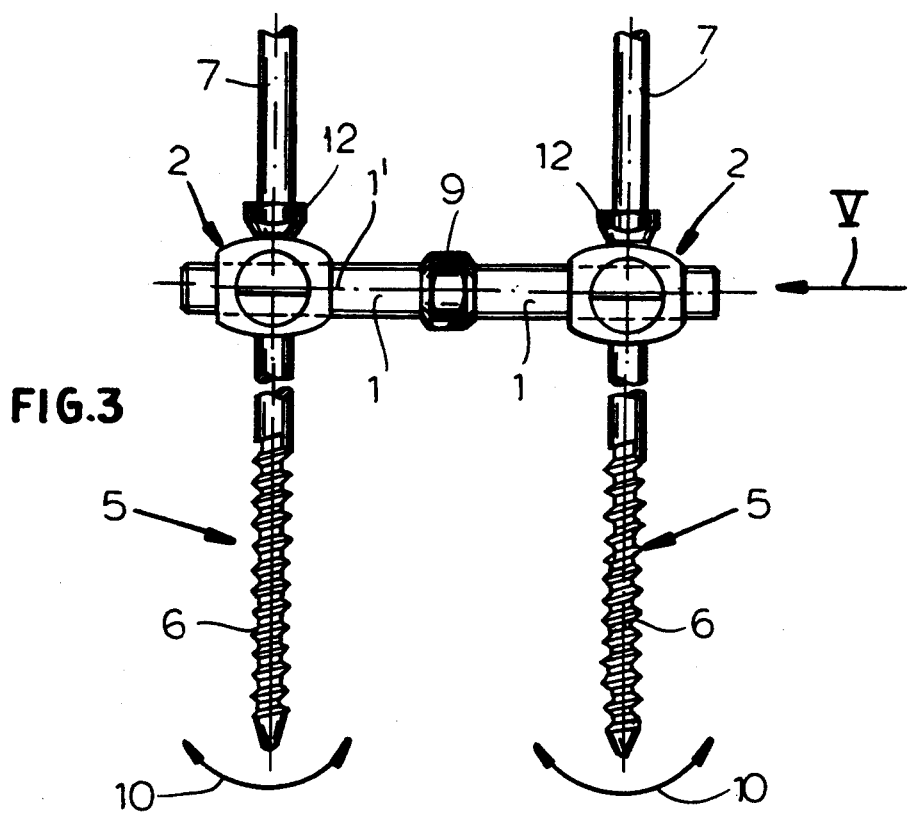
FIG. 3 is another embodiment of the implant in a representation corresponding to FIG. 1.
Figure 4:
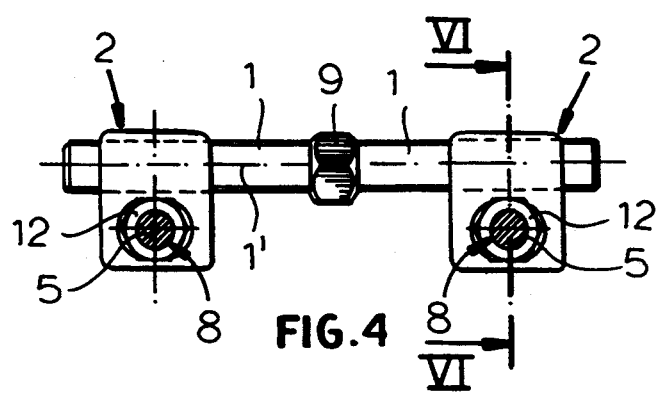
FIG. 4 is the implant according to FIG. 3 in a top view.
Figure 5:
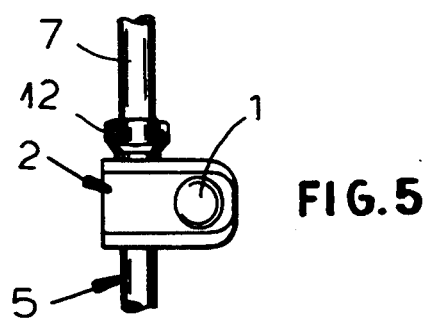
FIG. 5 is a frontal view of the implant according to FIGS. 1 to 4 in the direction of arrow V.

The implant according to FIGS. 3 to 5 differs from the implant according to FIGS. 1 and 2 basically only by that merely two connection pieces 2 are provided and that both their threaded spindles 1 are made in one piece. Between the two connection pieces 2 the threaded spindles are equipped again with a hexagon 9 for the common actuation with a key. On both sides of this hexagon, the threaded spindles 1 are threaded in opposite senses, which applies also to the nut threading of the two connection pieces 2. Therefore if the threaded spindle 1 made in one piece is turned, the two connection pieces 2 can either be moved towards each other or away from each other, corresponding to the sense of rotation.

The receiving element 8 for the resetting screws 5 in the connection pieces 2 have the same design in both implants. Thereby the resetting screws 5 are slidably guided in their respective receiving element 8 in the longitudinal direction of the screw with the threadless smooth shaft portion 7 and are also pivotable transversely thereto in the direction of arrow 10. In addition the receiving elements 8 are provided with a clamping device activated by a clamping member, which in the clamping state secures the resetting screws 5 against sliding, as well as pivoting in the receiving element 8. The clamping member is a threaded sleeve 11, which again is equipped with a hexagonal collar 12 for the actuation by key.

More detailed, in the connection piece 2 a pivot opening 13 for a link body 14 is formed, and in the link body 14 a guide channel 15 is shaped for the resetting screws 5. On both sides of the link body 14 the resetting screw 5 projects from the connection piece 2 through the openings 16 provided in the walling of the connection piece 2. The link body 14 is divided in two across the axis 17 of the guide channel 15 to form a gap 14a in the plane 18.

In one part 14.1 of the two parts 14.1 and 14.2 a conical seat 19 coaxial with the guide channel 15 is formed and in this seat a peripherally slotted clamping ring 20 is located.

In the braced state the clamping member, namely the threaded sleeve 11 forces the two link body parts 14.1, 14.2 in the pivot opening 13 against the opening surface 13' on the one hand and on the other hand it forces the clamping ring 20 in the conical seat 19 against the resetting screws 5. This is achieved in a simple manner due to the fact that the conical seat 19 abuts with its enlarged end in the plane 18 between the two link body parts 14.1, 14.2 and that the link body part 14.2 which is opposite to this abutment is provided with a threaded bore 21 coaxial with the guide channel 15, wherein the threaded sleeve 11 which forms a segment of the guide channel 15 is guided.

The threaded sleeve 11 pushes with the sleeve end 22 lying within the link body 14 against the clamping ring 20 in the conical seat 19 and with the other sleeve end projects outwardly with the hexagon collar 12 positioned there through the opening 16, so that the hexagon collar 12 is accessible for the actuation of the threaded sleeve 11.

The clamping ring 20 has an outer conical surface 23 suited to fit the conical seat 19. The rim 24 of the clamping ring 20 has an outer diameter at least as large as the one of the ends 22 of the threaded sleeve 11. As a result the threaded sleeve always rests against the facing rim 24 of the clamping ring 20. When the threaded sleeve 11 is tightened, the clamping ring 20 in the conical seat 19 is braced against threadless shaft portion 7 of the resetting screw 5; at the same time, due to the threaded sleeves 11 resting against the clamping ring 20, the two link body parts 14.1, 14.2 are pushed apart and are thereby locked in pivot opening 13.

The link body 14 and the pivot opening 13 are cylindrically shaped with a cylinder axis 25 being perpendicular to the axis 17 of the guide channel 15. The pivotability of the link body only about this sole axis 25 is sufficient in the case of the embodiment examples, since the connection pieces 2 themselves are rotatable about the axis of the spindles guiding them, and for this reason are capable to adjust to the inclination of the resetting screws 5 in the direction of this rotation on the guide spindle 1. In principle, in the case of implants with a differently designed guidance system of the connection pieces 2, it is of course possible to provide pivot openings and corresponding link bodies, for instance ball joint bodies, which can perform also a rotation about two axis perpendicular with respect to each other. However, in this case the construction of the receiving element 8 is more expensive. In the present case of only cylindrical link bodies there is a particularly simple way to insure that a very efficient locking of the link body 14 in the pivot opening 13 and thereby a fixation of the resetting screws 5 secured against pivoting is achieved. For this purpose on both sides of guide channel 15, at the outer peripheral surfaces of the link body 14, annular grooves 26 are formed coaxially with the cylinder axis 25 with peripherally slotted spring rings 27 being embedded therein, provided on the outside with crossribbing 28 and projecting radially with the ribs slightly over the peripheral cylinder surface 29 of the link body 14. This crossribbing 28 is achieved in a simple manner by providing the spring ring 27 with a threading.

If during the actuation of the threaded sleeve 11 the two link body parts 14.1, 14.2 are pushed apart, they are braced against the pivot opening surface 13' of the pivot opening 13 via ring springs 27, whereby their ribs embed themselves in the pivot opening surface 13' on the one hand and in the walling of the annular grooves 26 on the other hand.

I claim:

1. An implant for fixation of bones comprising:
   at least two connection pieces;
   means for adjusting a distance between the two connection pieces, each of the connection pieces being formed with a respective throughgoing pivot opening formed with a support peripheral surface;
   a respective link body in each pivot opening provided with a guide channel extending along a channel axis, the link body being split into two parts across the channel axis;
   a respective conical seat formed in one of the two parts along each of the guide channels;
   a respective resetting screw extending through each guide channel and projecting axially from opposite sides of the link body and having an end thereof engageable in a bone, the link body being pivotal about a pivot axis perpendicular to the channel axis with the resetting screw;
   a respective peripherally slotted clamping ring surrounding the resetting screw in the guide channel and juxtaposed with the seat; and
   a respective clamping member displaceable along the guide channel and bracing the parts of the link body against the support surface and the clamping ring against the seat and against the resetting screw in a clamping position of the clamping member, blocking thereby the resetting screw against axial sliding and against pivoting about the pivot axis.

2. The implant defined in claim 8 wherein the two parts are spaced apart in the clamping position of the clamping member, forming thereby a gap therebetween, an enlarged outer end of the conical seat adjoining the gap, the other one of the two parts of the link body being formed with a threaded axial bore threadedly receiving the clamping member, said clamping member being formed with an externally threaded sleeve to be axially guided along the guide channel toward the clamping position of the clamping member, the clamping member being formed with a respective inner end engaging the ring within the pivot opening and with an outer end projecting from a wall of the connecting piece and provided with means for actuating the clamping member.

3. The implant defined in claim 1 wherein the clamping ring is formed with:
   a respective conical peripheral surface formed complementary with the conical seat, and
   an outer rim facing the inner end of the clamping member and having a diameter at least as large as a diameter of the inner end of the clamping member.

4. The implant defined in claim 1 wherein the pivot opening and the link body are cylindrically shaped and coaxial with common cylinder axis extending perpendicular to the channel axis of the guide channel, the pivot axis, the link body being formed with an outer periphery formed with a pair of spaced apart annular grooves coaxial with the pivot axis, each groove receiving a respective peripherally slotted spring ring formed with a respective crossribbing projecting radially over the outer periphery of the link body.

5. The implant defined in claim 4 wherein the crossribbing is threads formed on the spring ring.

6. The implant defined in claim 4 wherein means for adjusting a distance between the two connection pieces includes a spindle formed with a spindle axis extending perpendicular to said pivot axis.

* * * * *